(12) United States Patent
Maki et al.

(10) Patent No.: US 11,896,751 B2
(45) Date of Patent: Feb. 13, 2024

(54) ADJUSTING DEVICE FOR PRESSURE DETECTOR

(71) Applicant: Nikkiso Company Limited, Tokyo (JP)

(72) Inventors: Hideto Maki, Shizuoka (JP); Shinya Hasegawa, Shizuoka (JP); Yuki Eda, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 883 days.

(21) Appl. No.: 16/928,504

(22) Filed: Jul. 14, 2020

(65) Prior Publication Data
US 2020/0338254 A1 Oct. 29, 2020

Related U.S. Application Data

(63) Continuation of application No. PCT/JP2019/001545, filed on Jan. 18, 2019.

(30) Foreign Application Priority Data

Jan. 18, 2018 (JP) ................................. 2018-006600

(51) Int. Cl.
*A61M 1/36* (2006.01)
*A61M 1/16* (2006.01)
(Continued)

(52) U.S. Cl.
CPC ............ *A61M 1/3639* (2013.01); *A61M 1/16* (2013.01); *A61M 60/279* (2021.01); *G01L 7/08* (2013.01)

(58) Field of Classification Search
CPC .... A61M 1/3639; A61M 1/16; A61M 60/279; A61M 2205/70; A61M 2205/07; G01L 7/08; G01L 27/002
See application file for complete search history.

(56) References Cited

U.S. PATENT DOCUMENTS 8,092,414 B2 1/2012 Schnell et al.
8,960,010 B1 2/2015 Crnkovich et al.
(Continued)

FOREIGN PATENT DOCUMENTS

EP 0330891 A1 9/1989
EP 1078642 A2 2/2001
(Continued)

OTHER PUBLICATIONS

European Search Report of the corresponding European Application No. 19 740 982.4, dated Aug. 31, 2021.
(Continued)

*Primary Examiner* — Francis C Gray
(74) *Attorney, Agent, or Firm* — Young Basile Hanlon & MacFarlane, P.C.

(57) ABSTRACT

An adjusting device for a pressure detector that is capable of arbitrarily adjusting the initial position of a membrane member is provided. An adjusting device for a pressure detector includes a control unit that sequentially executes a first step in which a predetermined adjusting pressure is generated in a first zone by activating a pump with the first zone being closed by the closing of an electromagnetic valve, and a second step in which a gas-phase portion, the first zone, and a second zone are combined into a closed space by disabling the closing of the electromagnetic valve; and an adjusting-pressure-acquiring unit that acquires the adjusting pressure to be generated in the first step, the adjusting pressure being acquired in accordance with a relationship between a pressure and a capacity of the first zone in the first step and a pressure and a capacity of the combination of the gas-phase portion, the first zone, and the second zone in the second step. The control unit brings the membrane member to a position corresponding to the adjusting pressure by executing the second step after activating the
(Continued)

pump in the first step in such a manner as to generate the adjusting pressure acquired by the adjusting-pressure-acquiring unit.

13 Claims, 13 Drawing Sheets

(51) Int. Cl.
*G01L 7/08* (2006.01)
*A61M 60/279* (2021.01)

(56) References Cited

U.S. PATENT DOCUMENTS

| | | | | |
|---|---|---|---|---|
| 9,907,897 | B2* | 3/2018 | Burbank | A61M 1/1656 |
| 10,058,694 | B2* | 8/2018 | Norris | A61M 1/159 |
| 10,443,591 | B2* | 10/2019 | Wilt | A61M 1/15625 |
| 11,478,578 | B2* | 10/2022 | Farrell | F04B 53/10 |
| 11,725,645 | B2* | 8/2023 | Wilt | F04B 9/109 |
| | | | | 210/646 |
| 2003/0115965 | A1 | 6/2003 | Mittelstein et al. | |
| 2005/0069425 | A1* | 3/2005 | Gray | F04B 43/067 |
| | | | | 417/390 |
| 2007/0118153 | A1 | 5/2007 | Funamura et al. | |
| 2007/0295093 | A1 | 12/2007 | Reiter et al. | |
| 2016/0231192 | A1* | 8/2016 | Hammerschmidt | G01L 9/0072 |
| 2017/0312412 | A1 | 11/2017 | Mochizuki | |
| 2017/0340798 | A1 | 11/2017 | Lindley et al. | |
| 2018/0080843 | A1 | 3/2018 | Funamura et al. | |
| 2022/0236127 | A1* | 7/2022 | Ishizaki | A61M 1/1609 |

FOREIGN PATENT DOCUMENTS

| | | | | |
|---|---|---|---|---|
| EP | 2974868 | A1 | 1/2016 | |
| JP | 2003033430 | A | 2/2003 | |
| WO | 2009072390 | A1 | 6/2009 | |
| WO | 2010/009867 | A1 | 1/2010 | |
| WO | 2014/028103 | A1 | 2/2014 | |
| WO | 2014/093846 | A1 | 6/2014 | |
| WO | 2015/099932 | A1 | 7/2015 | |
| WO | 2016/092848 | A1 | 6/2016 | |
| WO | WO-2016092848 | A1 * | 6/2016 | A61M 1/14 |

OTHER PUBLICATIONS

Potentially related U.S. Appl. No. 15/823,794, filed Nov. 28, 2017, published as 2018/0080843.

* cited by examiner

[Fig. 1]
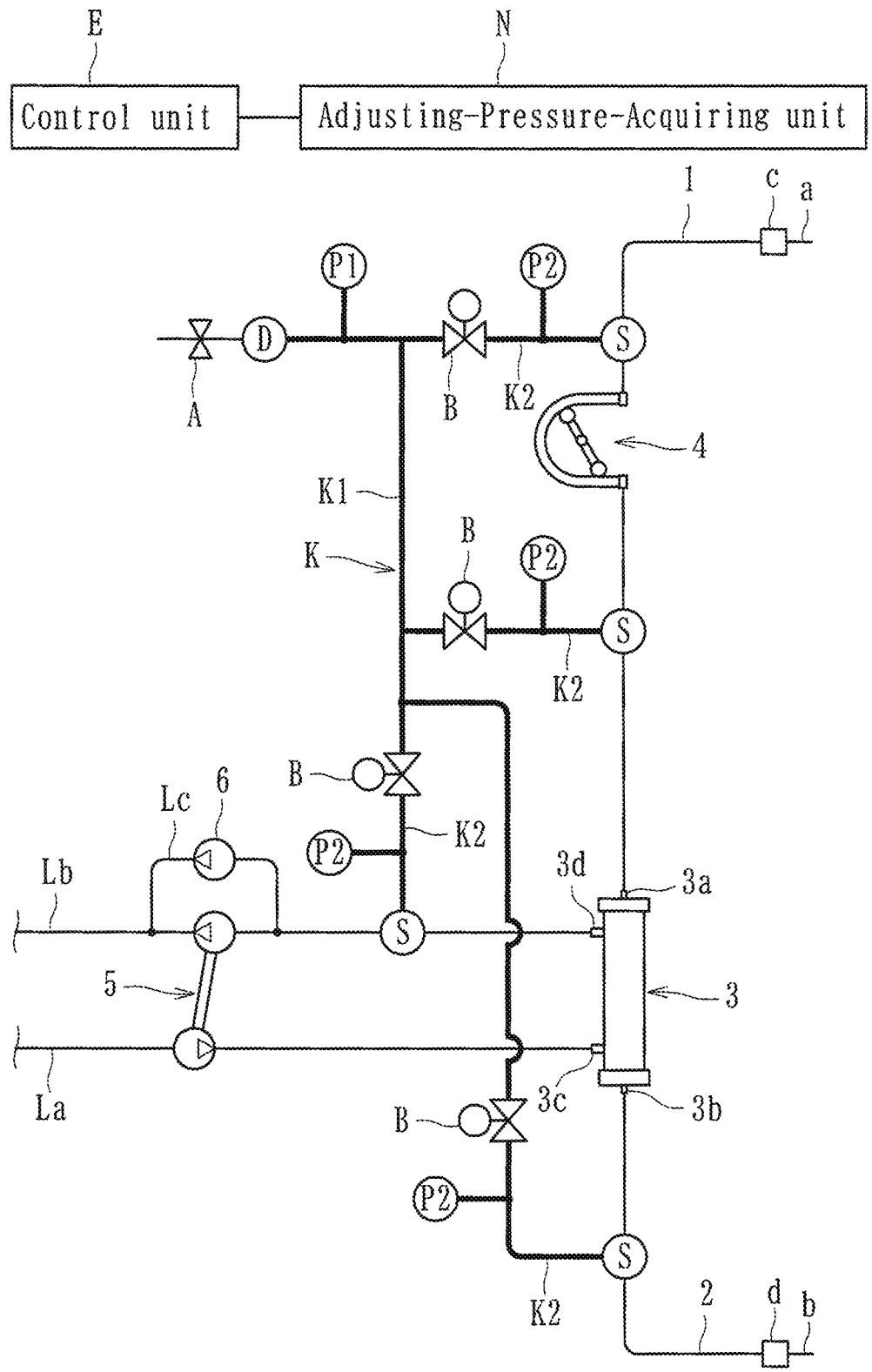

[Fig. 2]
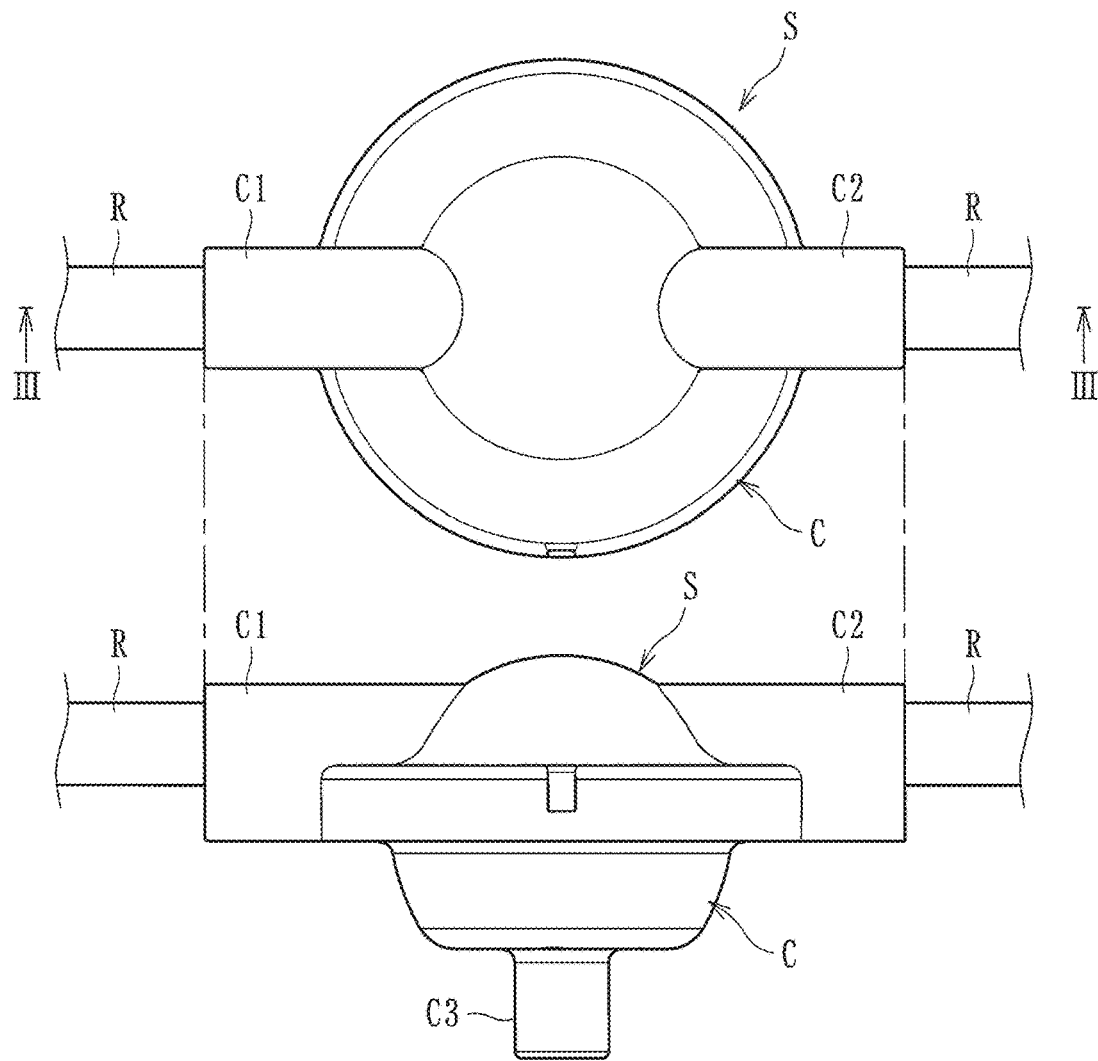
[Fig. 3]
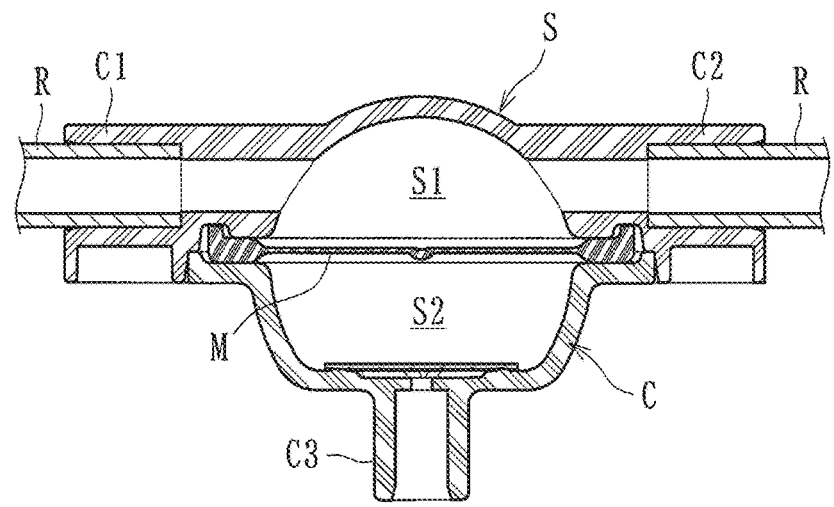

[Fig. 4]
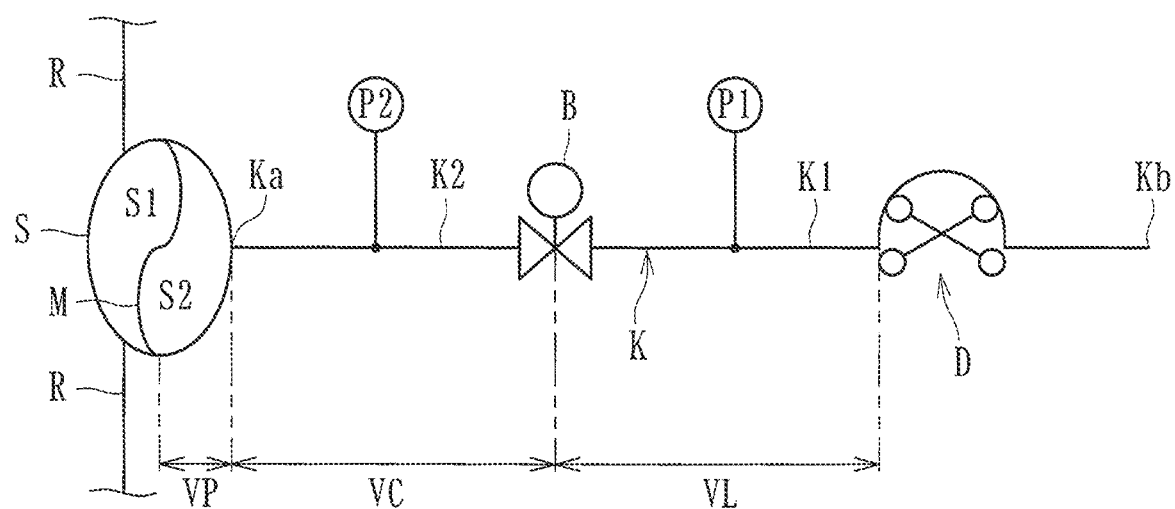

[Fig. 5]
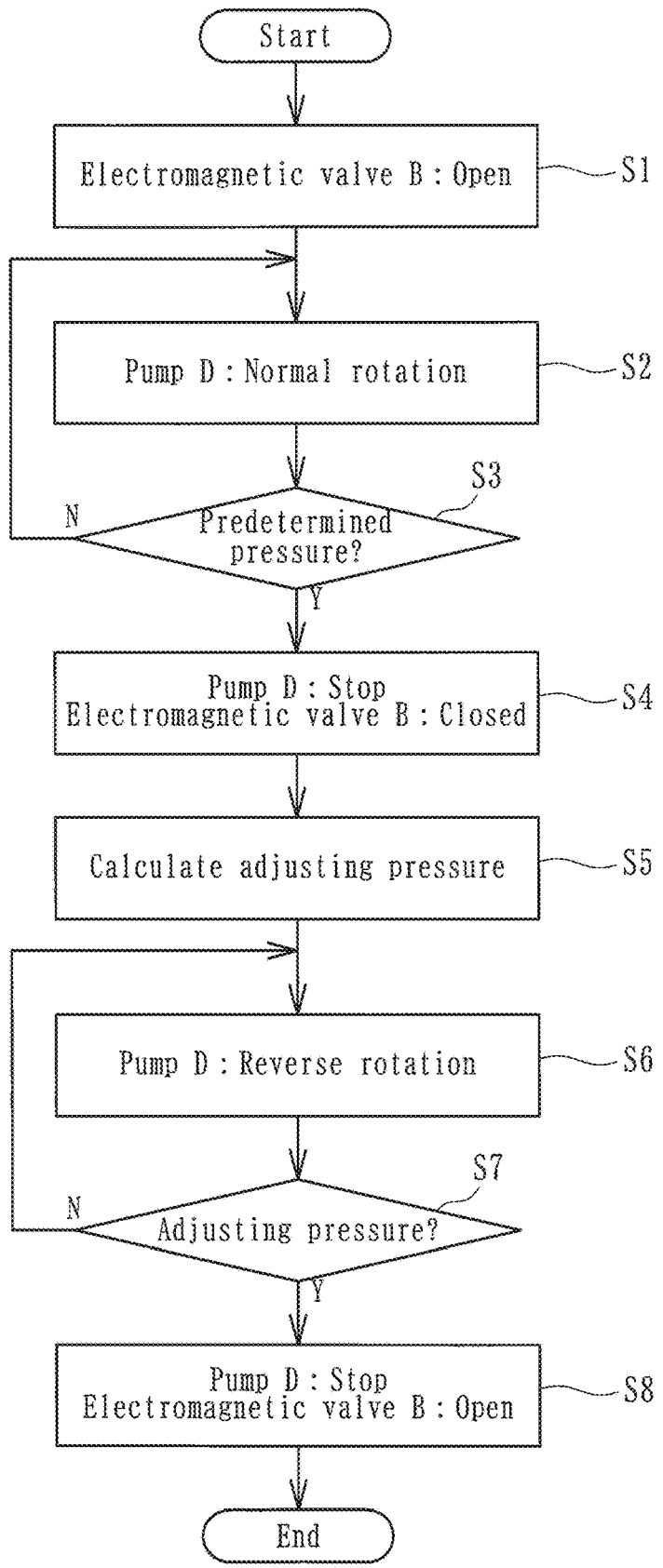

[Fig. 6]
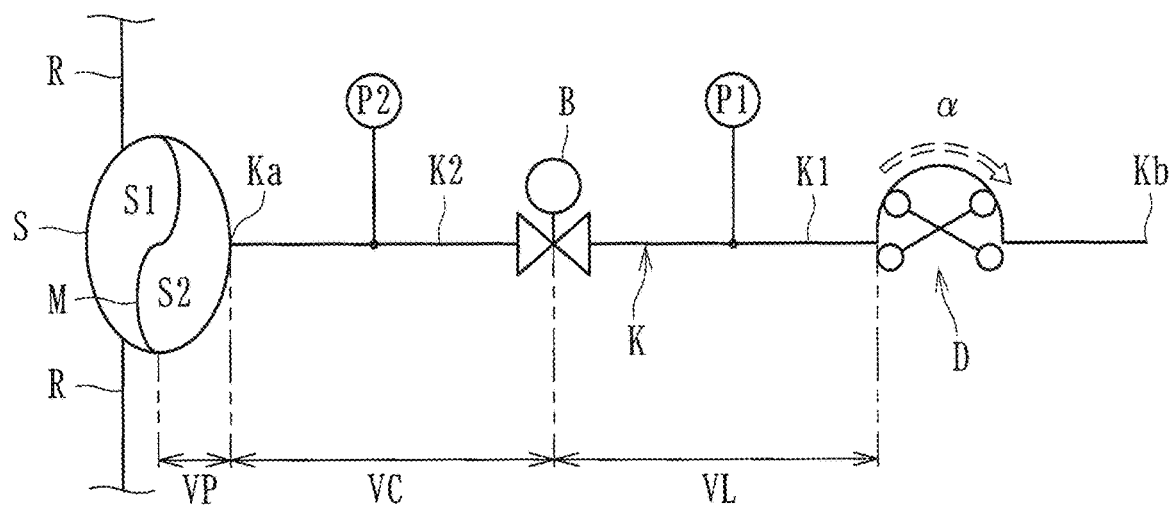
[Fig. 7]
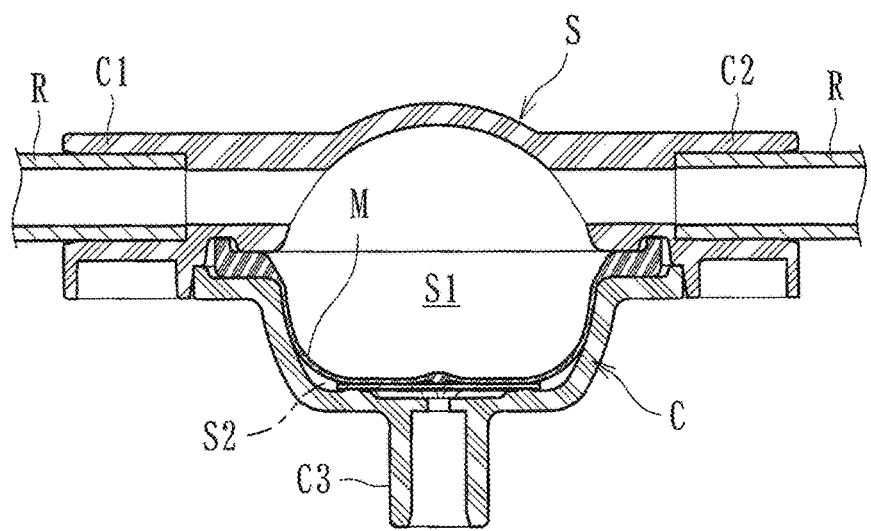

[Fig. 8]
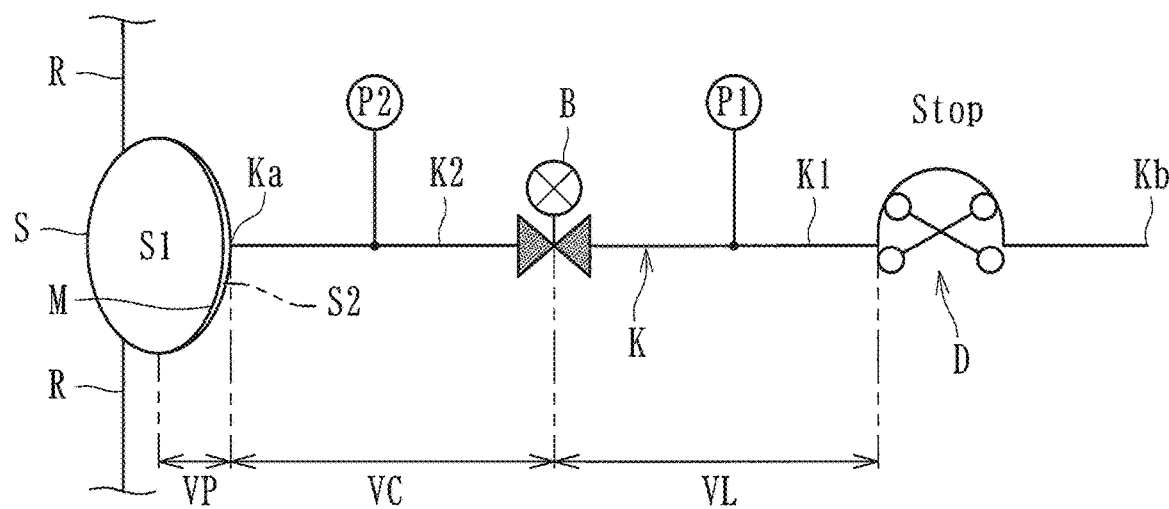
[Fig. 9]
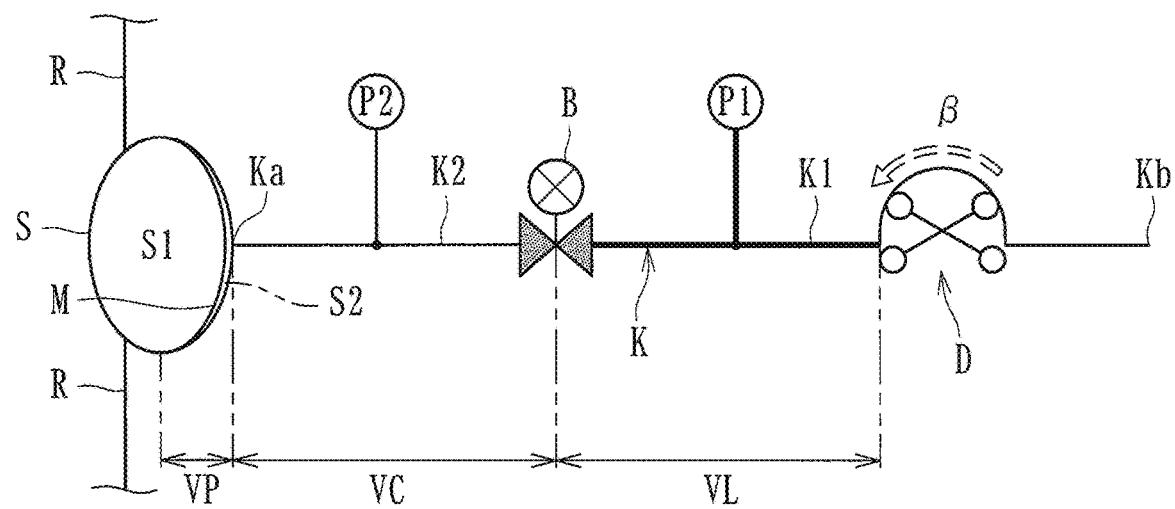

[Fig. 10]
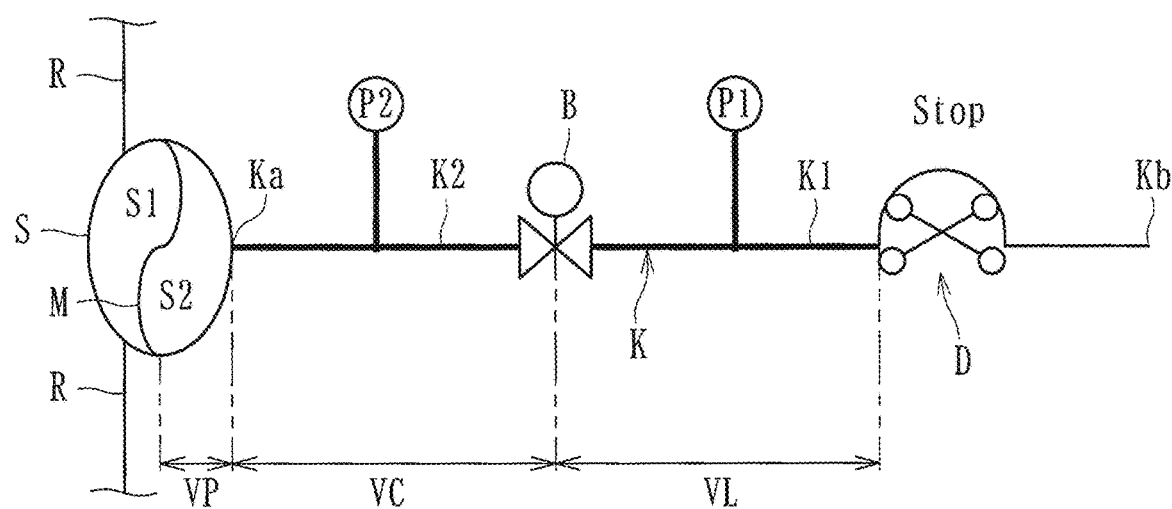

[Fig. 11]
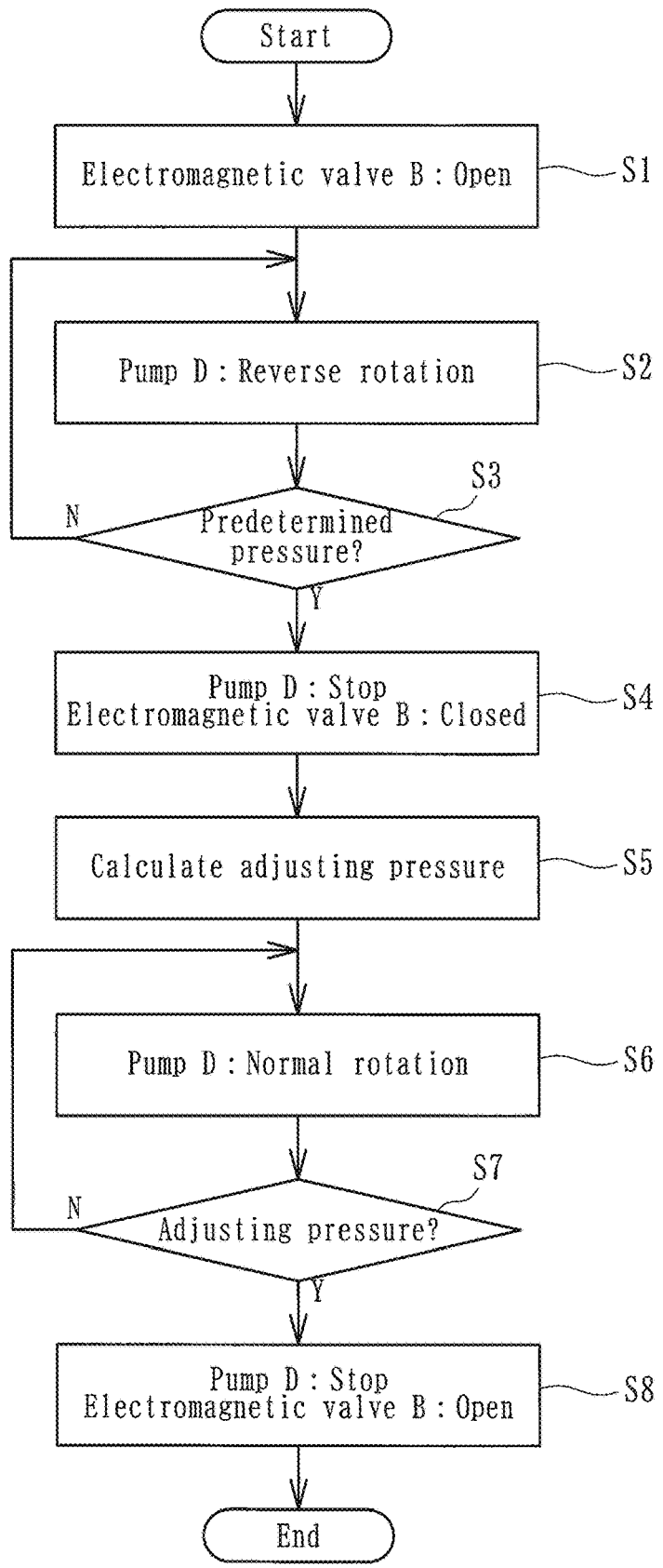

[Fig. 12]
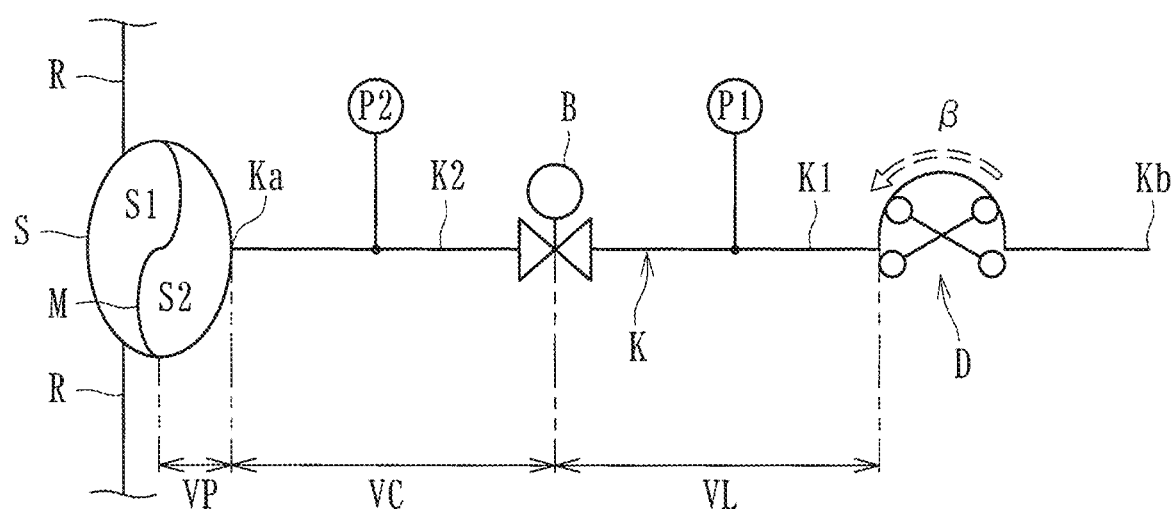
[Fig. 13]
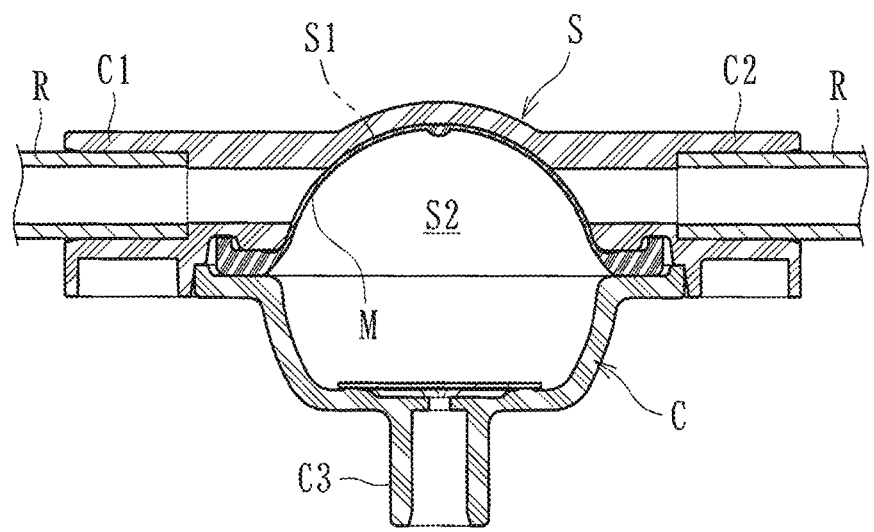

[Fig. 14]
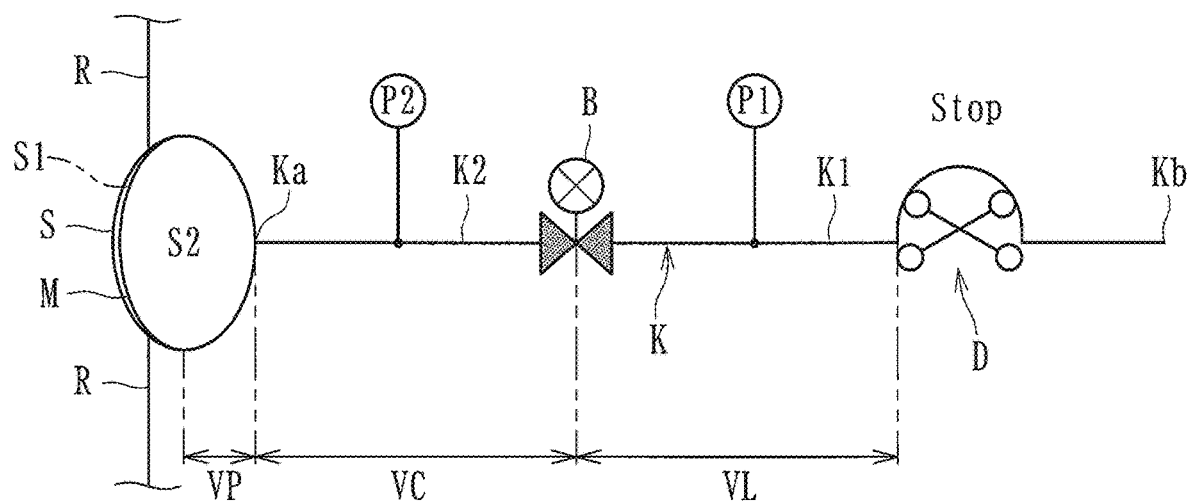
[Fig. 15]
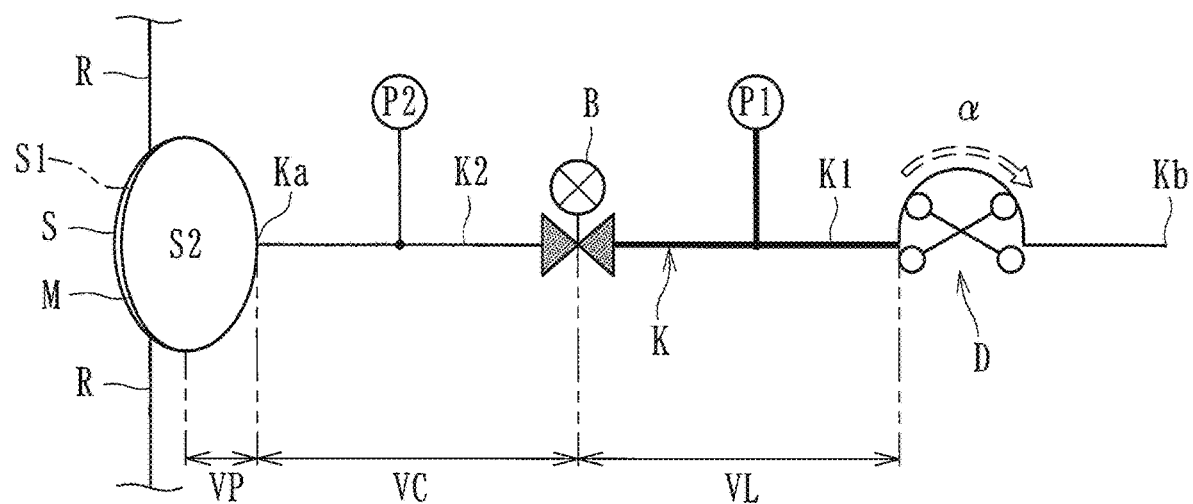

[Fig. 16]
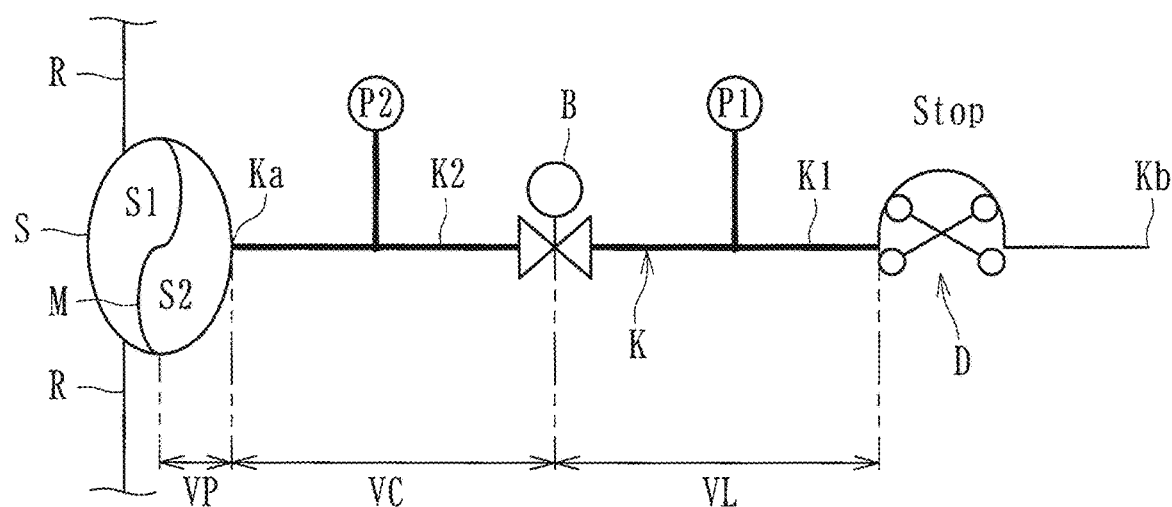

[Fig. 17]
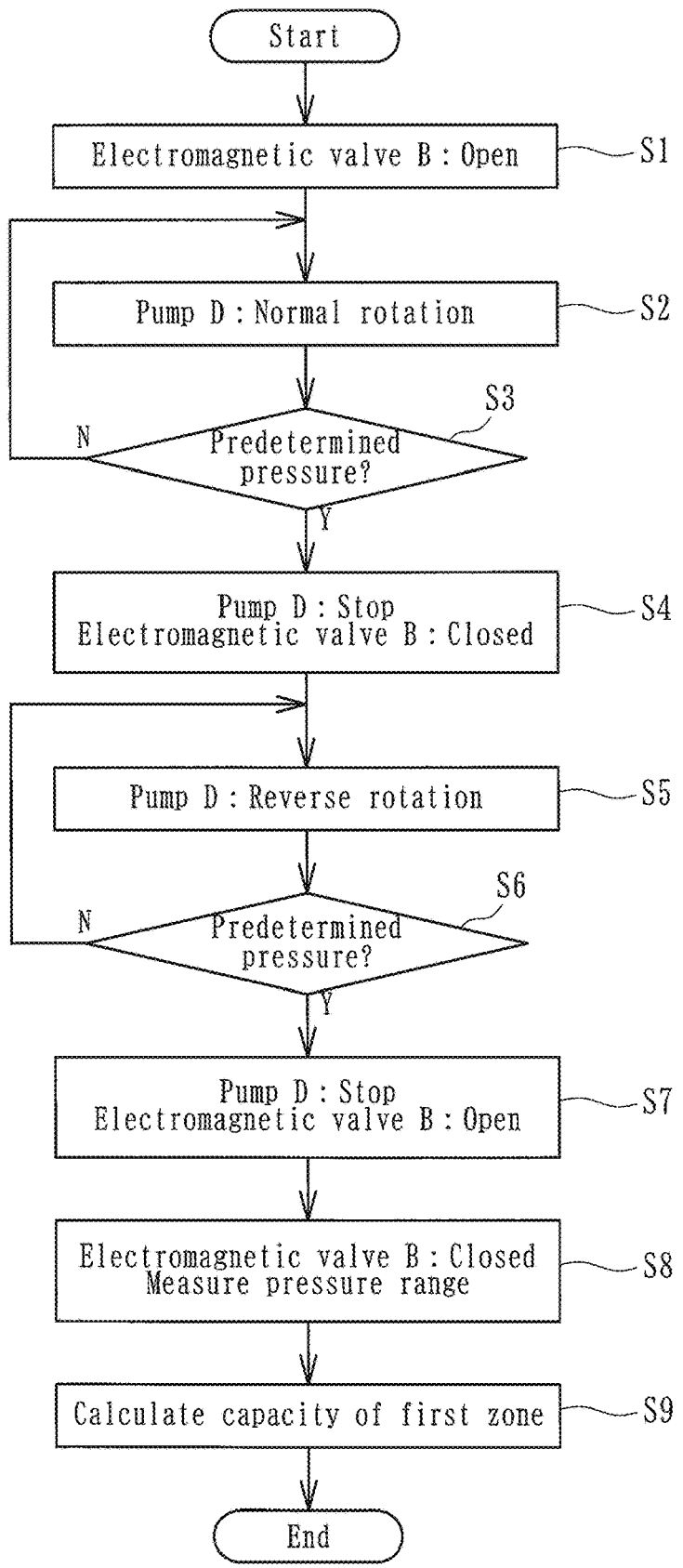

[ Fig. 18 ]
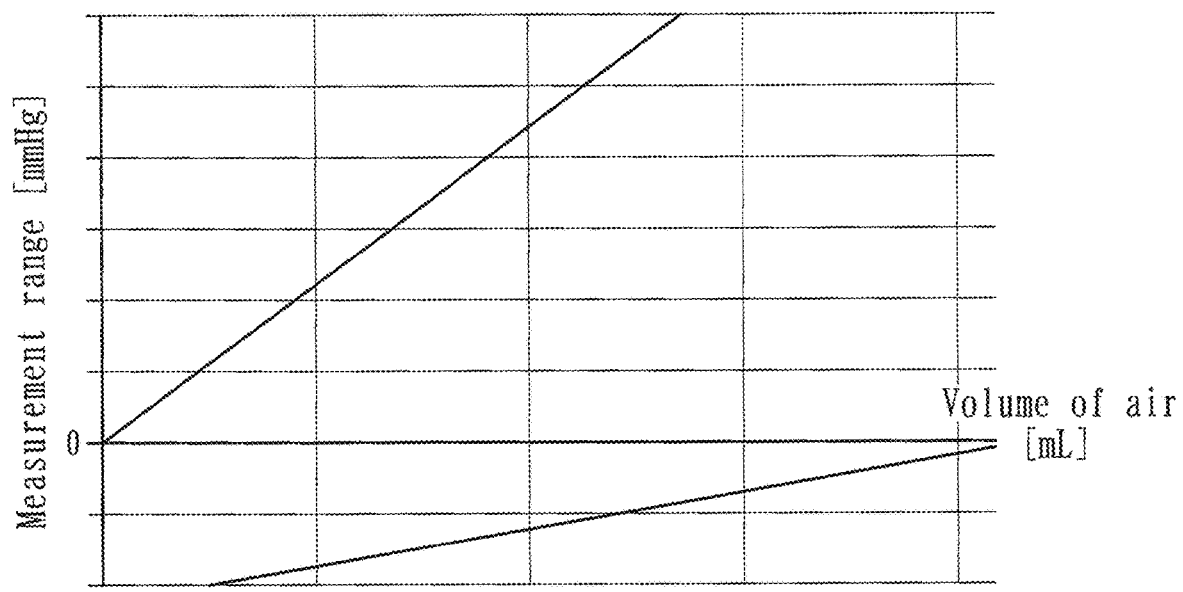

ADJUSTING DEVICE FOR PRESSURE DETECTOR

CROSS-REFERENCE TO RELATED APPLICATION(S)

This application is a continuation of International Application No. PCT/JP2019/001545, filed on Jan. 18, 2019, which claims priority to Japanese Application No. 2018-006600, filed on Jan. 18, 2018, the entire disclosures of which are hereby incorporated by reference.

FIELD

The present teachings relates to an adjusting device for a pressure detector capable of detecting the pressure of liquid in a flow route by detecting the pressure in a gas-phase portion.

BACKGROUND

In general, dialysis treatment is performed by using a blood circuit for allowing blood collected from a patient to extracorporeally circulate and return into the body. Such a blood circuit basically includes, for example, an arterial blood circuit and a venous blood circuit that are connectable to a dialyzer (a blood purifier) including hollow fiber membranes. The arterial blood circuit and the venous blood circuit are attached to distal ends thereof with an arterial puncture needle and a venous puncture needle, respectively. The patient is punctured with the puncture needles, and extracorporeal circulation of blood in the dialysis treatment is performed.

Hitherto, pressure detectors for detecting the pressure of blood that extracorporeally circulates through a blood circuit have been proposed. For example, a pressure detector disclosed by PTL 1 includes a case connectable to a blood circuit, and a diaphragm (a membrane member) provided in the case and separating a liquid-phase portion to be supplied with blood in the blood circuit and a gas-phase portion to be supplied with air from each other, the diaphragm being displaceable in accordance with the pressure of the blood supplied into the liquid-phase portion. The pressure detector is capable of detecting the pressure of the blood by detecting the pressure in the gas-phase portion with a pressure sensor. With the above known pressure detector, since the liquid-phase portion and the gas-phase portion are separated from each other by the membrane member, the pressure of the blood in the blood circuit can be detected accurately while the blood is prevented from coming into contact with the air in the gas-phase portion.

PTL 1: JP2017-504389 (a Published Japanese Translation of a PCT Application), the teachings of which are expressly incorporated by reference herein for all purposes.

SUMMARY

However, the above known pressure detector has the following problem.

The membrane member for separating the gas-phase portion and the liquid-phase portion from each other in the case is a soft member because the membrane member needs to be displaced in accordance with the pressure of the liquid (the hydraulic pressure) in the liquid-phase portion. Therefore, in a state before use where some air is present in the liquid-phase portion, the initial position of the membrane member is instable. Hence, in the state before use, if the membrane member is not positioned in the center of the case but, for example, near the wall of the liquid-phase portion, the range of measurable negative pressure (minus pressure) (the measurement range) is narrowed. In contrast, if the membrane member is positioned near the wall of the gas-phase portion, the range of measurable positive pressure (plus pressure) (the measurement range) is narrowed.

In a pressure detector to be attached to a part where mainly the negative pressure is desired to be measured, if the initial position of the membrane member is set close to the wall of the gas-phase portion, the measurement range of negative pressure can be widened. On the other hand, in a pressure detector to be attached to a part where the positive pressure is desired to be measured, if the initial position of the membrane member is set close to the wall of the liquid-phase portion, the measurement range for positive pressure can be widened. Accordingly, there has been a demand for the capability of arbitrarily adjusting the initial position of the membrane member in accordance with the part where the pressure detector is to be attached.

The present teachings have been conceived in view of the above circumstances and provides an adjusting device for a pressure detector that is capable of arbitrarily adjusting the initial position of a membrane member.

Variation 1 comprises an adjusting device for a pressure detector, the pressure detector including a case connectable to a flow route for liquid, and a membrane member attached to the case and separating a liquid-phase portion to be supplied with the liquid in the flow route and a gas-phase portion to be supplied with gas from each other, the membrane member being displaceable in accordance with a pressure of the liquid supplied into the liquid-phase portion, the pressure detector detecting the pressure of the liquid in the flow route by detecting a pressure in the gas-phase portion. The adjusting device includes piping having one end and an other end, the one end serving as a connecting portion connectable to the gas-phase portion, the other end allowing the gas to be introduced into or discharged from the piping; a pump that introduces or discharges the gas into or from a portion of the flow route in the piping and the gas-phase portion through the other end of the piping, the piping and the gas-phase portion being connected to each other through the connecting portion; a closing unit capable of closing a predetermined position of the flow route in the piping and separating the flow route in the piping into a first zone nearer to the other end and a second zone nearer to the one end by the closing; a control unit capable of controlling the pump and the closing unit and that sequentially executes a first step in which a predetermined adjusting pressure is generated in the first zone by activating the pump with the first zone being closed by the closing of the closing unit, and a second step in which the gas-phase portion, the first zone, and the second zone are combined into a closed space by disabling the closing of the closing unit; and an adjusting-pressure-acquiring unit that acquires the adjusting pressure to be generated in the first step, the adjusting pressure being acquired in accordance with a relationship between a pressure and a capacity of the first zone in the first step and a pressure and a capacity of the combination of the gas-phase portion, the first zone, and the second zone in the second step. The control unit brings the membrane member to a position corresponding to the adjusting pressure by executing the second step after activating the pump in the first step in such a manner as to generate the adjusting pressure acquired by the adjusting-pressure-acquiring unit.

Variation 2 may comprise the adjusting device for the pressure detector according to Variation 1, the relationship of pressure and capacity is based on Boyle-Charles' law.

Variation 3 may comprise the adjusting device for the pressure detector according to Variation 1 or 2, the control unit sequentially executes the first step and the second step after executing a close-contact step in which the membrane member is brought into close contact with an inner peripheral wall of the gas-phase portion or an inner peripheral wall of the liquid-phase portion by activating the pump such that the gas is introduced into or discharged from the gas-phase portion.

Variation 4 may comprise the adjusting device for the pressure detector according to any of Variation 1-3, further includes a first pressure-detecting unit that detects a pressure in the first zone.

Variation 5 may comprise the adjusting device for the pressure detector according to any of Variation 1-4, further includes a second pressure-detecting unit that detects a pressure in the second zone, in addition to the first pressure-detecting unit.

Variation 6 may comprise the adjusting device for the pressure detector according to any of Variation 1-5, the pump is a peristaltic pump capable of sending the gas by squeezing the piping in a lengthwise direction of the piping.

Variation 7 may comprise the adjusting device for the pressure detector according to any of Variation 1-6, the adjusting-pressure-acquiring unit calculates the adjusting pressure in accordance with the relationship between the pressure and the capacity of the first zone in the first step and the pressure and the capacity of the combination of the gas-phase portion, the first zone, and the second zone in the second step.

Variation 8 may comprise the adjusting device for the pressure detector according to any of Variation 1-7, the adjusting-pressure-acquiring unit calculates an actual capacity of the first zone or the second zone in accordance with the relationship between the pressure and the capacity of the first zone in the first step and the pressure and the capacity of the combination of the gas-phase portion, the first zone, and the second zone in the second step.

Variation 9 may comprise the adjusting device for the pressure detector according to any of Variation 1-8, the adjusting device for the pressure detector includes the control unit capable of controlling the pump and the closing unit and that sequentially executes the first step in which a predetermined adjusting pressure is generated in the first zone by activating the pump with the first zone being closed by the closing of the closing unit, and the second step in which the gas-phase portion, the first zone, and the second zone are combined into a closed space by disabling the closing of the closing unit; and the adjusting-pressure-acquiring unit that acquires the adjusting pressure to be generated in the first step, the adjusting pressure being acquired in accordance with the relationship between the pressure and the capacity of the first zone in the first step and the pressure and the capacity of the combination of the gas-phase portion, the first zone, and the second zone in the second step. The control unit brings the membrane member to the position corresponding to the adjusting pressure by executing the second step after activating the pump in the first step in such a manner as to generate the adjusting pressure acquired by the adjusting-pressure-acquiring unit. Therefore, the initial position of the membrane member can be adjusted arbitrarily.

Variation 10 may comprise the adjusting device for the pressure detector according to any of Variation 1-9, the relationship of pressure and capacity is based on Boyle-Charles' law. Therefore, the adjusting pressure can be calculated with a relatively simple mathematical expression.

Variation 11 may comprise the adjusting device for the pressure detector according to any of Variation 1-10, the control unit sequentially executes the first step and the second step after executing the close-contact step in which the membrane member is brought into close contact with the inner peripheral wall of the gas-phase portion or the inner peripheral wall of the liquid-phase portion by activating the pump such that the gas is introduced into or discharged from the gas-phase portion. Therefore, the membrane member can be fixed to the inner peripheral wall in the close-contact step, so that the membrane member can be prevented from being displaced in the first step to be executed thereafter.

Variation 12 may comprise the adjusting device for the pressure detector according to any of Variation 1-11, the adjusting device for the pressure detector further includes the first pressure-detecting unit that detects the pressure in the first zone. Therefore, the adjusting pressure can be accurately generated in the first zone in the first step in accordance with the pressure detected by the first pressure-detecting unit.

Variation 13 may comprise the adjusting device for the pressure detector according to any of Variation 1-12, the adjusting device for the pressure detector further includes the second pressure-detecting unit that detects the pressure in the second zone, in addition to the first pressure-detecting unit. Therefore, after the pressure detection for adjusting the initial position of the membrane member is executed by using the first pressure-detecting unit, the pressure of the liquid can be detected by using the second pressure-detecting unit.

In such a case, when the piping is closed by using the closing unit, the space communicating with the gas-phase portion can be limited to the second zone, and the pressure in the second zone can be detected by using the second pressure-detecting unit. Therefore, in the detection of the pressure of the liquid, changes in the pressure can be detected quickly in accordance with the displacement of the membrane member. Accordingly, the response can be improved. Furthermore, since the pressure of the liquid can be detected by using the second pressure-detecting unit while the second zone is closed, the first zone can be shared among a plurality of pressure detectors in the adjustment of the initial position of the membrane member.

Variation 14 may comprise the adjusting device for the pressure detector according to any of Variation 1-13, the pump is a peristaltic pump capable of sending the gas by squeezing the piping in the lengthwise direction of the piping. Therefore, the piping can be closed by stopping the pump. Accordingly, no separate closing unit for closing the first zone in the first step is necessary.

Variation 15 may comprise the adjusting device for the pressure detector according to any of Variation 1-14, the adjusting-pressure-acquiring unit calculates the adjusting pressure in accordance with the relationship between the pressure and the capacity of the first zone in the first step and the pressure and the capacity of the combination of the gas-phase portion, the first zone, and the second zone in the second step. Therefore, no preparation of a table or the like is necessary, and the initial position of the membrane member can be adjusted easily.

Variation 16 may comprise the adjusting device for the pressure detector according to any of Variation 1-15, the adjusting-pressure-acquiring unit calculates the actual capacity of the first zone or the second zone in accordance with the relationship between the pressure and the capacity of the first zone in the first step and the pressure and the capacity of the combination of the gas-phase portion, the first zone, and the second zone in the second step. Therefore, in bringing the membrane member to a given initial position, the influence that may be brought by the dimensional error of the first zone or the second zone can be reduced. Consequently, the accuracy can be improved.

BRIEF DESCRIPTION OF THE DRAWINGS

FIG. 1 is a schematic diagram illustrating a dialysis apparatus (a blood purification apparatus) to which an adjusting device for a pressure detector according to a variation of the present teachings is applied.

FIG. 2 includes a plan view and a side view of the pressure detector.

FIG. 3 is a sectional view taken along line illustrated in FIG. 2.

FIG. 4 is a schematic diagram illustrating an outline of the adjusting device for the pressure detector.

FIG. 5 is a flow chart illustrating a control process to be executed by the adjusting device for the pressure detector according to the first variation of the present teachings.

FIG. 6 is a schematic diagram illustrating a state of the adjusting device for the pressure detector in a close-contact step.

FIG. 7 is a schematic sectional diagram illustrating a state of a membrane member in the close-contact step.

FIG. 8 is a schematic diagram illustrating a state of the adjusting device for the pressure detector after the close-contact step and before a first step.

FIG. 9 is a schematic diagram illustrating a state of the adjusting device for the pressure detector in the first step.

FIG. 10 is a schematic diagram illustrating a state of the adjusting device for the pressure detector in a second step.

FIG. 11 is a flow chart illustrating a control process to be executed by an adjusting device for a pressure detector according to a second variation of the present teachings.

FIG. 12 is a schematic diagram illustrating a state of the adjusting device for the pressure detector in a close-contact step.

FIG. 13 is a schematic sectional diagram illustrating a state of a membrane member in the close-contact step.

FIG. 14 is a schematic diagram illustrating a state of the adjusting device for the pressure detector after the close-contact step and before a first step.

FIG. 15 is a schematic diagram illustrating a state of the adjusting device for the pressure detector in the first step.

FIG. 16 is a schematic diagram illustrating a state of the adjusting device for the pressure detector in a second step.

FIG. 17 is a flow chart illustrating a control process to be executed by an adjusting device for a pressure detector according to another variation of the present teachings.

FIG. 18 is a graph to be used in the control process executed by the adjusting device for the pressure detector.

DETAILED DESCRIPTION

Variations of the present teachings will now be described specifically with reference to the drawings.

A blood purification apparatus according to a first variation is a dialysis apparatus for giving dialysis treatment and includes, as illustrated in FIG. 1, a blood circuit including an arterial blood circuit 1 and a venous blood circuit 2, a dialyzer 3 (a blood purifier) connected to a proximal end of the arterial blood circuit 1 and to a proximal end of the venous blood circuit 2 and that purifies blood flowing through the blood circuit, a blood pump 4, a duplex pump 5, an ultrafiltration pump 6, pressure detectors S, piping K, a pump D, electromagnetic valves B (closing units), a control unit E, and an adjusting-pressure-acquiring unit N. A combination of the piping K, the pump D, each of the electromagnetic valves B (the closing units), the control unit E, and the adjusting-pressure-acquiring unit N serves as an adjusting device for a corresponding one of the pressure detectors S according to the present variation.

The arterial blood circuit 1 is provided with an arterial puncture needle a connected to a distal end thereof through a connector c, and with the blood pump 4, which is a peristaltic pump, at a halfway position thereof. On the other hand, the venous blood circuit 2 is provided with a venous puncture needle b connected to a distal end thereof through a connector d. When the blood pump 4 is activated while a patient is punctured with the arterial puncture needle a and the venous puncture needle b, the patient's blood flows through the arterial blood circuit 1 and reaches the dialyzer 3, where the blood is purified. Then, the blood flows through the venous blood circuit 2 and returns into the patient's body.

That is, blood purification treatment is performed by purifying the patient's blood with the dialyzer 3 while causing the blood to extracorporeally circulate through the blood circuit from the distal end of the arterial blood circuit 1 to the distal end of the venous blood circuit 2. In this specification, the side of the puncture needle for blood removal (blood collection) is referred to as the "arterial" side, and the side of the puncture needle for blood return is referred to as the "venous" side. The "arterial" side and the "venous" side are not defined in accordance with which of the artery and the vein is to be the object of puncture.

The dialyzer 3 has, in a housing thereof, a blood inlet 3a (a blood introduction port), a blood outlet 3b (a blood delivery port), a dialysate inlet 3c (an inlet of a dialysate flow route: a dialysate introduction port), and a dialysate outlet 3d (an outlet of the dialysate flow route: a dialysate delivery port). The blood inlet 3a is connected to the proximal end of the arterial blood circuit 1. The blood outlet 3b is connected to the proximal end of the venous blood circuit 2. The dialysate inlet 3c and the dialysate outlet 3d are connected to a dialysate introduction line La and a dialysate drain line Lb, respectively, extending from a dialysis-apparatus body.

The dialyzer 3 houses a plurality of hollow fibers (not illustrated). The hollow fibers form blood purification membranes for purifying the blood. The blood purification membranes in the dialyzer 3 define blood flow routes (each extending between the blood inlet 3a and the blood outlet 3b) through which the patient's blood flows and dialysate flow routes (each extending between the dialysate inlet 3c and the dialysate outlet 3d) through which dialysate flows. The hollow fibers forming the blood purification membranes each have a number of very small holes (pores) extending therethrough from the outer peripheral surface to the inner peripheral surface, thereby forming a hollow fiber membrane. Impurities and the like contained in the blood are allowed to permeate through the membranes into the dialysate.

The duplex pump 5 is provided over the dialysate introduction line La and the dialysate drain line Lb in the dialysis-apparatus body. The dialysate drain line Lb is provided with a bypass line Lc that bypasses the duplex pump 5. The bypass line Lc is provided with the ultrafiltration pump 6 for removing water from the patient's blood flowing through the dialyzer 3. One end of the dialysate introduction line La is connected to the dialyzer 3 (the dialysate inlet 3c), and the other end is connected to a dialysate supply device (not illustrated) that prepares a dialysate at a predetermined concentration. One end of the dialysate drain line Lb is connected to the dialyzer 3 (the dialysate outlet 3d), and the other end is connected to a drainage device, not illustrated. The dialysate supplied from the dialysate supply device flows through the dialysate introduction line La into the dialyzer 3, and further flows through the dialysate drain line Lb into the drainage device.

Pressure detectors S are connected to the blood circuit according to the present variation. The pressure detectors S are connected to respective positions between the distal end (the connector c) of the arterial blood circuit 1 and a part where the blood pump 4 is provided, between the blood pump 4 and the dialyzer 3, and between the distal end (the connector d) of the venous blood circuit 2 and the position where the dialyzer 3 is provided, so that the pressure of the blood flowing through the arterial blood circuit 1 and the venous blood circuit 2 can be detected.

Specifically, as illustrated in FIGS. 2 and 3, the pressure detectors S each include a case C connectable to a corresponding one of flow routes R for liquid (corresponding to the arterial blood circuit 1 or the venous blood circuit 2 in the present variation), and a membrane member M attached to the case C and separating a liquid-phase portion S1 to be supplied with the liquid in the flow route (the blood in the arterial blood circuit 1 or the venous blood circuit 2 in the present variation) and a gas-phase portion S2 to be supplied with gas from each other, the membrane member M being displaceable in accordance with the pressure of the liquid (blood) supplied into the liquid-phase portion S1. Thus, the pressure detector S is capable of detecting the pressure of the liquid in the flow route R (the arterial blood circuit 1 or the venous blood circuit 2) by detecting the pressure in the gas-phase portion S2 with a pressure-detecting unit (a first pressure-detecting unit P1 or a second pressure-detecting unit P2).

The case C is a hollow molded component obtained by molding a predetermined resin material or the like. The case C has connection ports C1 and C2 integrally molded therewith. The connection ports C1 and C2 are connectable to the flow route R for the liquid and allow the flow route R to communicate with the liquid-phase portion S1. The case C further has a connection port C3 integrally molded therewith. The connection port C3 is connectable to one end Ka (see FIG. 4) of the piping K, to be described below, and allows the one end Ka to communicate with the gas-phase portion S2. A space provided in the case C is separated (sectioned) by the membrane member M into the liquid-phase portion S1 and the gas-phase portion S2. The membrane member M is a diaphragm attached to the case C and is made of a flexible material that is displaceable or deformable in conformity with pressure change occurring in the liquid-phase portion S1 or the gas-phase portion S2.

Accordingly, the present variation employs an adjusting device for adjusting the initial position of the membrane member M included in each of the pressure detectors S connected to respective desired positions of the blood circuit. The adjusting device for each pressure detector S includes the piping K, the pump D, a corresponding one of the electromagnetic valves B as the closing unit, the first pressure-detecting unit P1 (or the second pressure-detecting unit P2), the control unit E, and the adjusting-pressure-acquiring unit N.

The piping K is formed of flow routes made of tubes or the like through which air is allowed to flow. As illustrated in FIG. 4, the piping K has a connecting portion Ka at one end thereof. The connecting portion Ka is connected to and communicable with the gas-phase portion S2 in the case C. The piping K further has an atmosphere-releasing portion Kb at the other end thereof. The atmosphere-releasing portion Kb is open to the atmosphere. The piping K employed in the present variation is preferably made of hard resin or the like, which is less likely to deform with pressure change occurring therein. The pump D is a peristaltic pump capable of sending air by squeezing the piping K in the lengthwise direction of the piping K. The pump D is provided at a position of the piping K that is near the atmosphere-releasing portion Kb. When activated, the pump D can introduce or discharge air into and from the piping K and the gas-phase portion S2 through the atmosphere-releasing portion Kb (an other end).

The electromagnetic valve B as the closing unit is attached to a position of the piping K that is between the connecting portion Ka and the part where the pump D is provided. The electromagnetic valve B (the closing unit) is capable of arbitrarily closing a predetermined position of the flow route in the piping K and separating (sectioning) the flow route in the piping K into a first zone K1 nearer to the atmosphere-releasing portion Kb (nearer to the other end) and a second zone K2 nearer to the connecting portion Ka (nearer to the one end) by the closing. Specifically, when the electromagnetic valve B is activated to close the flow route with the part where the pump D is provided being closed by stopping the pump D, the first zone K1 can be separated from a combination of the gas-phase portion S2 and the second zone K2. That is, the two zones can each be closed (a hermetic state). Another closing unit A, such as an electromagnetic valve, is attached to the piping K between the part where the pump D is provided and the atmosphere-releasing portion Kb. However, the closing unit A may be omitted. The electromagnetic valve B may be replaced with another closing device (such as a clamping device).

The first pressure-detecting unit P1 is attached to a predetermined position of the first zone K1 and serves as a pressure sensor capable of detecting the pressure in at least the first zone (the pressure in a combination of the first zone K1 and any space communicating therewith). The second pressure-detecting unit P2 is attached to a predetermined position of the second zone K2 and serves as a pressure sensor capable of detecting the pressure in at least the second zone K2 (the pressure in a combination of the second zone K2 and any space communicating therewith).

The control unit E is a microcomputer or the like capable of controlling the pump D and the electromagnetic valve B (the closing unit). The control unit E sequentially executes a first step (see FIG. 9) in which a predetermined adjusting pressure is generated in the first zone K1 by rotating the pump D reversely (rotated in a direction β indicated in FIG. 9) with the first zone K1 being closed by closing the electromagnetic valve B; and a second step (see FIG. 10) in which the gas-phase portion S2, the first zone K1, and the second zone K2 are combined into a closed space by disabling the closing of the electromagnetic valve B with the pump D being stopped.

The adjusting-pressure-acquiring unit N acquires the adjusting pressure to be generated in the first step, which is executed for bringing the membrane member M to a given initial position in accordance with a relationship between a pressure and a capacity of the first zone K1 in the first step and a pressure and a capacity of the combination of the gas-phase portion S2, the first zone K1, and the second zone K2 in the second step. The adjusting-pressure-acquiring unit N is an arithmetic unit such as a microcomputer. The adjusting-pressure-acquiring unit N according to the present variation uses, as the relationship of pressure and capacity, a relationship based on Boyle-Charles' law (combined gas law) (a law regarding the volume, the pressure, and the temperature of ideal gas), particularly Boyle's law (in which if the temperature is constant, the pressure and the volume are inversely proportional to each other).

The control unit E according to the present variation is capable of bringing the membrane member M to a given initial position in the first step by activating the pump D in such a manner as to generate the adjusting pressure acquired (calculated) by the adjusting-pressure-acquiring unit N and then executing the second step. Specifically, in the first step, when the pump D is rotated reversely (rotated in the direction β in FIG. 9) with the first zone K1 being closed by closing the electromagnetic valve B, the pressure in the first zone K1 is accumulated until the adjusting pressure acquired (calculated) by the adjusting-pressure-acquiring unit N is reached. Subsequently, in the second step, the gas-phase portion S2, the first zone K1, and the second zone K2 are combined into a closed space by disabling the closing of the electromagnetic valve B with the pump D being stopped. Thus, the membrane member M can be brought to the given position (initial position).

Furthermore, as illustrated in FIG. 6, the control unit E according to the present variation executes a close-contact step in which air is discharged from the gas-phase portion S2 (that is, air in the space including the gas-phase portion S2 is released through the atmosphere-releasing portion Kb) by rotating the pump D normally (rotating in a direction α indicated in the drawing), thereby bringing the membrane member M into close contact with the inner peripheral wall of the gas-phase portion S2 (see FIG. 7). Subsequently, the control unit E sequentially executes the first step and the second step.

Now, a control process to be executed by the control unit E of the adjusting device for the pressure detector S according to the first variation will be described with reference to the flow chart illustrated in FIG. 5.

First, each one end (the connecting portion Ka) of the piping K is connected to the connection port C3 of a corresponding one of the pressure detectors S connected to the respective desired positions of the blood circuit. In the present variation, the closing unit A is kept open, and the puncture needles (a, b) are not attached to the distal end (the connector c) of the arterial blood circuit 1 and the distal end (the connector d) of the venous blood circuit 2. Thus, an atmosphere-released state is established. Therefore, at the start of the adjustment of the pressure detector S, some air is present in the liquid-phase portion S1, as well as in the gas-phase portion S2.

Then, as illustrated in FIG. 6, the electromagnetic valve B is opened (S1), and the pump D is rotated normally (rotated in the direction α) (S2), whereby, as illustrated in FIG. 7, air is discharged from the gas-phase portion S2 to bring the membrane member M into close contact with the inner peripheral wall of the gas-phase portion S2 (the close-contact step). After the above activation of the pump D, whether the value detected by the first pressure-detecting unit P1 (or the second pressure-detecting unit P2) has reached a predetermined pressure (in this case, a predetermined negative pressure close to the vacuum) is checked (S3). If it is determined that the predetermined pressure has been reached, the process proceeds to S4.

In S4, as illustrated in FIG. 8, the pump D is stopped, and the flow route is closed by closing the electromagnetic valve B, whereby a space as a combination of the gas-phase portion S2 and the second zone K2 and a space as the first zone K1 are produced as closed spaces respectively. Subsequently, the adjusting-pressure-acquiring unit N calculates the adjusting pressure (S5). The adjusting pressure is a value for bringing the membrane member M to a given initial position when the first step (S6 and S7) and the second step (S8) that are to be executed thereafter are executed sequentially. The value is determined in accordance with the relationship (the relationship based on Boyle-Charles' law) between the pressure and the capacity of the first zone K1 in the first step and the pressure and the capacity of the combination of the gas-phase portion S2, the first zone K1, and the second zone K2 in the second step.

That is, according to Boyle-Charles' law (or Boyle's law, because temperature T is constant), the adjusting pressure is calculable with the following mathematical expression:

$$Pt=((V_P+V_C+V_L)/V_L)\times P_M \quad \text{(Math. 1)}$$

(where Pt denotes the adjusting pressure as a target pressure in the first step, $P_M$ denotes the pressure in the liquid-phase portion S1 when the membrane member M is at a given initial position (in the present variation, 1 atm (760 mmHg) because the distal ends of the blood circuit are open to the atmosphere), $V_P$ denotes the capacity of the gas-phase portion S2 when the membrane member M is at the initial position, $V_C$ denotes the capacity of the second zone K2, and $V_L$ denotes the capacity of the first zone K1).

In the present variation, since the distal end (the connector c) of the arterial blood circuit 1 and the distal end (the connector d) of the venous blood circuit 2 are open to the atmosphere, 1 atm (760 mmHg) is inputted as PM, as described above. The atmospheric pressure is variable with the environment (such as orthometric height and/or weather) in which the adjusting device is installed. Therefore, not a fixed value (760 mmHg) but a value corresponding to the installation environment may be inputted as PM. Thus, the initial position of the membrane member M can be adjusted more accurately.

Subsequently, as illustrated in FIG. 9, the pump D is rotated reversely (rotated in the direction β) while the electromagnetic valve B is kept closed (S6), whereby air is introduced from the outside into the first zone K1, which is closed (the first step). With the above activation of the pump D, the pressure in the first zone K1 is accumulated, and whether the value detected by the first pressure-detecting unit P1 has reached the adjusting pressure calculated in advance by the adjusting-pressure-acquiring unit N is checked (S7). If it is determined that the adjusting pressure has been reached, the process proceeds to S8 (the second step).

In S8, as illustrated in FIG. 10, the pump D is stopped, and the electromagnetic valve B is opened to disable the closing of the flow route, whereby a space as a combination of the gas-phase portion S2, the second zone K2, and the first zone K1 is produced as a closed space (the second step). Consequently, the air accumulated in the first zone K1 in the first step is sent to the gas-phase portion S2. Thus, the membrane member M can be brought to the given initial position (the position targeted in Math. 1).

Through the above process, the membrane member M of the pressure detector S can be brought to the given initial position. Therefore, when the blood pump 4 is activated after the patient is punctured with the puncture needles (a, b) attached to the distal end of the arterial blood circuit 1 and the distal end of the venous blood circuit 2 respectively, extracorporeal circulation (blood removal) through the blood circuit is started such that desired blood purification treatment is given. In such extracorporeal circulation of blood, if the second zone K2 is closed to the first zone K1 by closing the electromagnetic valve B (the closing unit), the second pressure-detecting unit P2 is allowed to detect the pressure of the blood in the blood circuit.

A variation of the present teachings will be described.

A blood purification apparatus according to the present variation is a dialysis apparatus for giving dialysis treatment, as with the case of the first variation, and includes, as illustrated in FIG. 1, a blood circuit including an arterial blood circuit 1 and a venous blood circuit 2, a dialyzer 3 (a blood purifier) connected to a proximal end of the arterial blood circuit 1 and to a proximal end of the venous blood circuit 2 and that purifies blood flowing through the blood circuit, a blood pump 4, a duplex pump 5, an ultrafiltration pump 6, pressure detectors S, piping K, a pump D, electromagnetic valves B (closing units), a control unit E, and an adjusting-pressure-acquiring unit N. A combination of the piping K, the pump D, each of the electromagnetic valves B (the closing units), the control unit E, and the adjusting-pressure-acquiring unit N serves as an adjusting device for a corresponding one of the pressure detectors S according to the present variation, which has the same configuration as in the first variation. Therefore, detailed description of elements that are the same as those described in the first variation is omitted.

The control unit E according to the present variation is a microcomputer or the like capable of controlling the pump D and the electromagnetic valve B (the closing unit). The control unit E sequentially executes a first step (see FIG. 15) in which a predetermined adjusting pressure is generated in the first zone K1 by rotating the pump D normally (rotated in a direction α indicated in FIG. 15) with the first zone K1 being closed by closing the electromagnetic valve B; and a second step (see FIG. 16) in which the gas-phase portion S2, the first zone K1, and the second zone K2 are combined into a closed space by disabling the closing of the electromagnetic valve B with the pump D being stopped.

The adjusting-pressure-acquiring unit N according to the present variation is capable of acquiring (calculating) the adjusting pressure to be generated in the first step, which is executed for bringing the membrane member M to a given initial position in accordance with a relationship between a pressure and a capacity of the first zone K1 in the first step and a pressure and a capacity of the combination of the gas-phase portion S2, the first zone K1, and the second zone K2 in the second step. The adjusting-pressure-acquiring unit N is an arithmetic unit such as a microcomputer. The adjusting-pressure-acquiring unit N according to the present variation uses, as the relationship of pressure and capacity, a relationship based on Boyle-Charles' law (combined gas law) (a law regarding the volume, the pressure, and the temperature of ideal gas), particularly Boyle's law (if the temperature is constant, the pressure and the volume are inversely proportional to each other).

The control unit E according to the present variation is capable of bringing the membrane member M to a given initial position in the first step by activating the pump D to generate the adjusting pressure calculated by the adjusting-pressure-acquiring unit N and then executing the second step. Specifically, in the first step, when the pump D is rotated normally (rotated in the direction α in FIG. 15) with the first zone K1 being closed by closing the electromagnetic valve B, the pressure in the first zone K1 is reduced until the adjusting pressure calculated by the adjusting-pressure-acquiring unit N is reached. Subsequently, in the second step, the gas-phase portion S2, the first zone K1, and the second zone K2 are combined into a closed space by disabling the closing of the electromagnetic valve B with the pump D being stopped. Thus, the membrane member M can be brought to the given position (initial position).

Furthermore, as illustrated in FIG. 12, the control unit E according to the present variation executes a close-contact step in which air is introduced into the gas-phase portion S2 (that is, air is taken into the space including the gas-phase portion S2 through the atmosphere-releasing portion Kb) by rotating the pump D reversely (rotating in the direction β in the drawing), thereby bringing the membrane member M into close contact with the inner peripheral wall of the liquid-phase portion S1 (see FIG. 13). Subsequently, the control unit E sequentially executes the first step and the second step.

Now, a control process to be executed by the control unit E of the adjusting device for the pressure detector S according to the second variation will be described with reference to the flow chart illustrated in FIG. 11.

First, each one end (the connecting portion Ka) of the piping K is connected to the connection port C3 of a corresponding one of the pressure detectors S connected to the respective desired positions of the blood circuit. In the present variation, the closing unit A is kept open, and the puncture needles (a, b) are not attached to the distal end (the connector c) of the arterial blood circuit 1 and the distal end (the connector d) of the venous blood circuit 2. Thus, an atmosphere-released state is established. Therefore, at the start of the adjustment of the pressure detector S, some air is present in the liquid-phase portion S1, as well as in the gas-phase portion S2.

Then, as illustrated in FIG. 12, the electromagnetic valve B is opened (S1), and the pump D is rotated reversely (rotated in the direction β) (S2), whereby, as illustrated in FIG. 13, air is introduced into the gas-phase portion S2 to bring the membrane member M into close contact with the inner peripheral wall of the liquid-phase portion S1 (the close-contact step). After the above activation of the pump D, whether the value detected by the first pressure-detecting unit P1 (or the second pressure-detecting unit P2) has reached a predetermined pressure (in this case, a predetermined positive pressure) is checked (S3). If it is determined that the predetermined pressure has been reached, the process proceeds to S4.

In S4, as illustrated in FIG. 14, the pump D is stopped, and the flow route is closed by closing the electromagnetic valve B, whereby a space as a combination of the gas-phase portion S2 and the second zone K2 and a space as the first zone K1 are produced as closed spaces. Subsequently, the adjusting-pressure-acquiring unit N calculates the adjusting pressure (S5). The adjusting pressure is a value for bringing the membrane member M to a given initial position when the first step (S6, S7) and the second step (S8) that are to be executed thereafter are executed sequentially. The value is determined in accordance with the relationship (the relationship based on Boyle-Charles' law) between the pressure and the capacity of the first zone K1 in the first step and the pressure and the capacity of the combination of the gas-phase portion S2, the first zone K1, and the second zone K2 in the second step.

That is, according to Boyle-Charles' law (or Boyle's law, because temperature T is constant), the adjusting pressure is calculable with the following mathematical expression:

$$Pt = ((V_P + V_C + V_L) \times P_M - (V_{POD} + V_C) \times P_P)/V_L \quad \text{(Math. 2)}$$

(where Pt denotes the adjusting pressure as a target pressure in the first step, $P_M$ denotes the pressure in the liquid-phase portion S1 when the membrane member M is at a given initial position (in the present variation, 1 atm (760 mmHg) because the distal ends of the blood circuit are open to the atmosphere), $V_P$ denotes the capacity of the gas-phase portion S2 when the membrane member M is at the initial position, $V_C$ denotes the capacity of the second zone K2, $V_L$ denotes the capacity of the first zone K1, $V_{PDO}$ denotes the total capacity of the gas-phase portion and the liquid-phase portion, and $P_P$ denotes the pressure (the predetermined pressure in S3) detected by the first pressure-detecting unit P1 when the membrane member M is brought into close contact with the inner peripheral wall of the liquid-phase portion S1).

Subsequently, as illustrated in FIG. 15, the pump D is rotated normally (rotated in the direction α) while the electromagnetic valve B is kept closed (S6), whereby air in the first zone K1, which is closed, is discharged to the outside (the first step). With the above activation of the pump D, the pressure in the first zone K1 is reduced, and whether the value detected by the first pressure-detecting unit P1 has reached the adjusting pressure calculated in advance by the adjusting-pressure-acquiring unit N is checked (S7). If it is determined that the adjusting pressure has been reached, the process proceeds to S8 (the second step).

In S8, as illustrated in FIG. 16, the pump D is stopped, and the electromagnetic valve B is opened to disable the closing of the flow route, whereby a space as a combination of the gas-phase portion S2, the second zone K2, and the first zone K1 is produced as a closed space (the second step). Consequently, the air in the combination of the gas-phase portion S2 and the second zone K2 is sent to the first zone K1 that has been depressurized in the first step. Thus, the membrane member M can be brought to the given initial position (the position targeted in Math. 2).

Through the above process, the membrane member M of the pressure detector S can be brought to the given initial position. Therefore, when the blood pump 4 is activated after the patient is punctured with the puncture needles (a, b) attached to the distal end of the arterial blood circuit 1 and the distal end of the venous blood circuit 2, extracorporeal circulation (blood removal) through the blood circuit is started such that desired blood purification treatment is given. In such extracorporeal circulation of blood, if the second zone K2 is closed to the first zone K1 by closing the electromagnetic valve B (the closing unit), the second pressure-detecting unit P2 is allowed to detect the pressure of the blood in the blood circuit.

According to each of the first variation and the second variation, the adjusting device for the pressure detector S includes the control unit E capable of controlling the pump D and the electromagnetic valve B (the closing unit) and that sequentially executes the first step in which a predetermined adjusting pressure is generated in the first zone K1 by activating the pump D with the first zone K1 being closed by closing the electromagnetic valve B, and the second step in which the gas-phase portion S2, the first zone K1, and the second zone K2 are combined into a closed space by disabling the closing of the electromagnetic valve B; and the adjusting-pressure-acquiring unit N that acquires the adjusting pressure to be generated in the first step that is executed for bringing the membrane member M to a given initial position, the adjusting pressure being acquired in accordance with a relationship between a pressure and a capacity of the first zone K1 in the first step and a pressure and a capacity of the combination of the gas-phase portion S2, the first zone K1, and the second zone K2 in the second step. The control unit E is capable of bringing the membrane member M to the given initial position by executing the second step after activating the pump D in the first step in such a manner as to generate the adjusting pressure calculated by the adjusting-pressure-acquiring unit N. Therefore, the initial position of the membrane member M can be adjusted arbitrarily.

In particular, the relationship of pressure and capacity is based on Boyle-Charles' law (Boyle's law). Therefore, the adjusting pressure can be calculated with a relatively simple mathematical expression. If the initial position of the membrane member M is to be adjusted in an environment where temperature fluctuation is significant, it is preferable that temperature T be defined as a parameter in the mathematical expression. Furthermore, the control unit E according to each of the above variations sequentially executes the first step and the second step after executing the close-contact step in which the membrane member M is brought into close contact with the inner peripheral wall of the gas-phase portion S2 or the inner peripheral wall of the liquid-phase portion S1 by activating the pump D such that air is introduced into or discharged from the gas-phase portion S2. Therefore, the membrane member M can be fixed to the inner peripheral wall in the close-contact step, so that the membrane member M can be prevented from being displaced in the first step to be executed thereafter.

In addition, according to each of the above variations, the adjusting-pressure-acquiring unit N calculates the adjusting pressure in accordance with the relationship between the pressure and the capacity of the first zone K1 in the first step and the pressure and the capacity of the combination of the gas-phase portion S2, the first zone K1, and the second zone K2 in the second step. Therefore, no preparation of a table or the like is necessary, and the initial position of the membrane member M can be adjusted easily. Note that while the adjusting-pressure-acquiring unit N according to each of the above variations calculates the adjusting pressure in accordance with the relationship between the sets of pressure and capacity of the first zone K1 and the second zone K2, the adjusting pressure may be acquired by referring to a table or the like prepared in advance.

The adjusting device for the pressure detector S further includes the first pressure-detecting unit P1 that detects the pressure in the first zone K1. Therefore, the adjusting pressure can be accurately generated in the first zone K1 in the first step in accordance with the pressure detected by the first pressure-detecting unit P1. The adjusting device for the pressure detector according to each of the above variations further includes the second pressure-detecting unit P2 capable of detecting the pressure in the second zone K2, in addition to the first pressure-detecting unit P1 capable of detecting the pressure in the first zone K1. Therefore, after the pressure detection for adjusting the initial position of the membrane member M is executed by using the first pressure-detecting unit P1, the pressure of the blood (liquid) can be detected by using the second pressure-detecting unit P2.

In such a case, when the piping K is closed by using the electromagnetic valve B, the space communicating with the gas-phase portion S2 can be limited to the second zone K2, and the pressure in the second zone K2 can be detected by using the second pressure-detecting unit P2. Therefore, in the detection of the pressure of the blood (liquid), changes in the pressure can be detected quickly in accordance with the displacement of the membrane member M. Accordingly, the response can be improved. Furthermore, since the pressure of the blood (liquid) can be detected by using the second pressure-detecting unit P2 while the second zone K2 is closed, the first zone K1 can be shared among a plurality of pressure detectors S in the adjustment of the initial position of the membrane member M.

Alternatively, the first pressure-detecting unit P1 may detect both the pressure in the first zone K1 for the adjustment of the initial position of the membrane member M and the blood pressure in the first zone K1 during the treatment. In such a case, since the first pressure-detecting unit P1 can be used in both the pressure detection for the adjustment of the initial position and the detection of blood pressure, the second pressure-detecting unit P2 may be omitted. Accordingly, a reduction in the number of components and a reduction in costs can be achieved.

The pump D according to each of the above variations is a peristaltic pump capable of sending air by squeezing the piping K in the lengthwise direction of the piping K. Therefore, the piping K can be closed by stopping the pump D. Accordingly, no separate closing unit for closing the first zone K1 in the first step is necessary. The pump D as a peristaltic pump may be replaced with another pump (such as a syringe pump). In that case, a separate closing (in each of the above variations, the closing unit A) to be provided at a position near the atmosphere-releasing portion Kb may be employed.

Another variation of the present teachings will be described.

The present variation concerns a process executed before the setting of the initial position of the membrane member M according to the first variation or the second variation and is based on the premise that the setting of the initial position (the close-contact step, the first step, the second step, and so forth) is to be executed. Specifically, the adjusting-pressure-acquiring unit N according to the present variation is capable of calculating an actual capacity of the first zone K1 or the second zone K2 in accordance with a relationship between a pressure and a capacity of the first zone K1 in the first step and a pressure and a capacity of the combination of the gas-phase portion S2, the first zone K1, and the second zone K2 in the second step.

A specific control process according to the present variation will now be described with reference to the flow chart illustrated in FIG. 17. Some of the drawings referred to in any of the first and other variations will also be referred to according to need.

First, each one end (the connecting portion Ka) of the piping K is connected to the connection port C3 of a corresponding one of the pressure detectors S connected to the respective desired positions of the blood circuit. In the present variation, the closing unit A is kept open, and the puncture needles (a, b) are not attached to the distal end (the connector c) of the arterial blood circuit 1 and the distal end (the connector d) of the venous blood circuit 2. Thus, an atmosphere-released state is established.

Then, as illustrated in FIG. 6, the electromagnetic valve B is opened (S1), and the pump D is rotated normally (rotated in the direction α) (S2), whereby, as illustrated in FIG. 7, air is discharged from the gas-phase portion S2 to bring the membrane member M into close contact with the inner peripheral wall of the gas-phase portion S2. After the above activation of the pump D, whether the value detected by the first pressure-detecting unit P1 (or the second pressure-detecting unit P2) has reached a predetermined pressure (in this case, a predetermined negative pressure close to the vacuum) is checked (S3). If it is determined that the predetermined pressure has been reached, the process proceeds to S4.

In S4, as illustrated in FIG. 8, the pump D is stopped, and the flow route is closed by closing the electromagnetic valve B, whereby a space as a combination of the gas-phase portion S2 and the second zone K2 and a space as the first zone K1 are produced as closed spaces respectively. Subsequently, as illustrated in FIG. 9, the pump D is rotated reversely (rotated in the direction β) while the electromagnetic valve B is kept closed (S5), whereby air is introduced from the outside into the first zone K1, which is closed. With the above activation of the pump D, the pressure in the first zone K1 is accumulated, and whether the value detected by the first pressure-detecting unit P1 has reached a predetermined pressure is checked (S6). If it is determined that the predetermined pressure has been reached, the process proceeds to S7.

In S7, as illustrated in FIG. 10, the pump D is stopped, and the electromagnetic valve B is opened to disable the closing of the flow route, whereby a space as a combination of the gas-phase portion S2, the second zone K2, and the first zone K1 is produced as a closed space. Consequently, the air accumulated in the first zone K1 in the first step is sent to the gas-phase portion S2. Then, after the electromagnetic valve B is closed, a given pressure is applied to the liquid-phase portion S1, whereby the range of measurable pressure (the pressure range) is detected (S8). In accordance with the pressure range, the capacity of the gas-phase portion S2 when the membrane member M is at the initial position is calculated (S9).

Specifically, the pressure range (mmHg) and the capacity (mL) of the gas-phase portion S2 when the membrane member M is at the initial position are in a relationship illustrated in FIG. 18. With reference to this relationship, the capacity of the gas-phase portion S2 can be calculated. Furthermore, according to Boyle-Charles' law (or Boyle's law, because temperature T is constant) representing the relationship between the state of the air accumulated in S5 and S6 and the state of the accumulated air released in S7, the following mathematical expression holds. Therefore, the actual capacity of the first zone K1 can be calculated with the following mathematical expression:

$$V\text{pump} = P\text{atm}/(P\text{accum} - P\text{atm}) \times (V\text{pod} + V\text{air})$$

(where Vpump denotes the actual capacity of the first zone K1, Vair denotes the capacity of the gas-phase portion S2 calculated from the pressure range, Vpod denotes the capacity (a design value) of the second zone K2, Paccum denotes the pressure (a predetermined pressure) of the air accumulated in S6, and Patm denotes the atmospheric pressure (760 mmHg)).

In the above mathematical expression, the actual capacity (Vpump) of the first zone K1 is calculated on an assumption that the capacity (Vpod) of the second zone K2 is a design value. Alternatively, the actual capacity (Vpod) of the second zone K2 may be calculated on an assumption that the capacity (Vpump) of the first zone K1 is a design value. In the present variation, the capacity of the first zone K1 is set to be extremely greater than the capacity of the second zone K2, and the influence that may be brought by an error in the capacity is significant. Therefore, it is preferable to calculate the actual capacity (Vpump) of the first zone K1 on an assumption that the capacity (Vpod) of the second zone K2 is a design value.

According to the above variation, the adjusting-pressure-acquiring unit N is capable of calculating the actual capacity of the first zone K1 or the second zone K2 in accordance with a relationship between a pressure and a capacity of the first zone K1 in the first step and a pressure and a capacity of the combination of the gas-phase portion, the first zone, and the second zone in the second step. Therefore, in bringing the membrane member M to a given initial position, the influence that may be brought by the dimensional error of the first zone K1 or the second zone K2 can be reduced. Consequently, the accuracy can be improved.

While some variations have been described above, the present teachings is not limited thereto. For example, the present teachings is applicable not only to an variation in which the distal end of the arterial blood circuit 1 and the distal end of the venous blood circuit 2 are open to the atmosphere but also to an variation in which the first step and the second step are executed with the distal ends being closed or connected to each other. In that case, $P_M$ in Math. 1 and Math. 2 needs to be a predetermined pressure value (a pressure expected at the time of use) of the liquid-phase portion S1.

The above variations each concern a case where the membrane member M is fixed by executing the close-contact step before the first step. Alternatively, the membrane member M may be fixed by any other method, without executing the close-contact step. The above variations each concern a case where the relationship of pressure and capacity to be used by the adjusting-pressure-acquiring unit N is based on Boyle-Charles' law (Boyle's law). Alternatively, any other relationship that is established by executing the first step and the second step may be used.

The other end of the piping K according to each of the above variations is open to the atmosphere. Alternatively, the other end of the piping K may be connected to a gas chamber or the like containing a predetermined gas (including gas other than air), as long as the gas can be introduced thereinto or discharged therefrom. In that case, the air to be introduced into or discharged from the gas-phase portion S2, the first zone K1, and the second zone K2 is replaced with another predetermined gas. The above variations each concern a case where a predetermined adjusting pressure is obtained by detecting the pressure in the flow route of the first zone K1 by using the first pressure-detecting unit P1. Alternatively, the amount of activation of the pump D (the number of revolutions or shots of the rotor or the like) that is necessary to generate a predetermined adjusting pressure may be stored in advance so that the pump D can be activated by that amount of activation in the first step. The above variations each concern a case where the object of measurement is the pressure of blood in a blood circuit of a blood purification apparatus. Alternatively, the adjusting device for the pressure detector S may measure any other liquid.

The present teachings is applicable to any adjusting device for a pressure detector that is in any other mode and for any other use, as long as the adjusting device includes a control unit capable of controlling a pump and a closing unit and that sequentially executes a first step in which a predetermined adjusting pressure is generated in a first zone by activating the pump with the first zone being closed by the closing of the closing unit, and a second step in which a gas-phase portion, the first zone, and a second zone are combined into a closed space by disabling the closing of the closing unit; and an adjusting-pressure-acquiring unit that acquires the adjusting pressure to be generated in the first step, the adjusting pressure being acquired in accordance with a relationship between a pressure and a capacity of the first zone in the first step and a pressure and a capacity of the combination of the gas-phase portion, the first zone, and the second zone in the second step, wherein the control unit is capable of bringing a membrane member to a given initial position by executing the second step after activating the pump in the first step in such a manner as to generate the adjusting pressure calculated by the adjusting-pressure-acquiring unit.

REFERENCE SIGN LIST 1 arterial blood circuit
2 venous blood circuit
3 dialyzer (blood purifier)
4 blood pump
5 duplex pump
6 ultrafiltration pump
La dialysate introduction line
Lb dialysate drain line
C case
M membrane member
S pressure detector
S1 liquid-phase portion
S2 gas-phase portion
K piping
K1 first zone (piping)
K2 second zone (piping)
Ka connecting portion (one end)
Kb atmosphere-releasing portion (other end)
D pump
B electromagnetic valve (closing unit)
P1 first pressure-detecting unit
P2 second pressure-detecting unit
E control unit
N adjusting-pressure-acquiring unit

The invention claimed is:

1. An adjusting device for a pressure detector, the pressure detector including
   a case connectable to a flow route for liquid, and
   a membrane member attached to the case and separating a liquid-phase portion to be supplied with the liquid in the flow route and a gas-phase portion to be supplied with gas from each other, the membrane member being displaceable in accordance with a pressure of the liquid supplied into the liquid-phase portion,
   the pressure detector detecting the pressure of the liquid in the flow route by detecting a pressure in the gas-phase portion,
the adjusting device comprising:
   piping having one end and an other end, the one end serving as a connecting portion connectable to the gas-phase portion, the other end allowing the gas to be introduced into or discharged from the piping;
   a pump that introduces or discharges the gas into or from a portion of the flow route in the piping and the gas-phase portion through the other end of the piping, the piping and the gas-phase portion being connected to each other through the connecting portion;
   a closing unit capable of closing a predetermined position of the flow route in the piping and separating the flow route in the piping into a first zone nearer to the other end and a second zone nearer to the one end by the closing;
   a control unit capable of controlling the pump and the closing unit and that sequentially executes a first step in which a predetermined adjusting pressure is generated in the first zone by activating the pump with the first zone being closed by the closing of the closing unit, and a second step in which the gas-phase portion, the first zone, and the second zone are combined into a closed space by disabling the closing of the closing unit; and an adjusting-pressure-acquiring unit that acquires the adjusting pressure to be generated in the first step, the adjusting pressure being acquired in accordance with a relationship between a pressure and a capacity of the first zone in the first step and a pressure and a capacity of the combination of the gas-phase portion, the first zone, and the second zone in the second step, wherein the control unit brings the membrane member to a position corresponding to the adjusting pressure by executing the second step after activating the pump in the first step in such a manner as to generate the adjusting pressure acquired by the adjusting-pressure-acquiring unit.

2. The adjusting device for the pressure detector according to claim 1, wherein the relationship of pressure and capacity is based on Boyle-Charles' law.

3. The adjusting device for the pressure detector according to claim 1, wherein the control unit sequentially executes the first step and the second step after executing a close-contact step in which the membrane member is brought into close contact with an inner peripheral wall of the gas-phase portion or an inner peripheral wall of the liquid-phase portion by activating the pump such that the gas is introduced into or discharged from the gas-phase portion.

4. The adjusting device for the pressure detector according to claim 1, further comprising a first pressure-detecting unit that detects a pressure in the first zone.

5. The adjusting device for the pressure detector according to claim 4, further comprising a second pressure-detecting unit that detects a pressure in the second zone, in addition to the first pressure-detecting unit.

6. The adjusting device for the pressure detector according to claim 1, wherein the pump is a peristaltic pump capable of sending the gas by squeezing the piping in a lengthwise direction of the piping.

7. The adjusting device for the pressure detector according to claim 1, wherein the adjusting-pressure-acquiring unit calculates the adjusting pressure in accordance with the relationship between the pressure and the capacity of the first zone in the first step and the pressure and the capacity of the combination of the gas-phase portion, the first zone, and the second zone in the second step.

8. The adjusting device for the pressure detector according to claim 1, wherein the adjusting-pressure-acquiring unit calculates an actual capacity of the first zone or the second zone in accordance with the relationship between the pressure and the capacity of the first zone in the first step and the pressure and the capacity of the combination of the gas-phase portion, the first zone, and the second zone in the second step.

9. The adjusting device for the pressure detector according to claim 2, wherein the control unit sequentially executes the first step and the second step after executing a close-contact step in which the membrane member is brought into close contact with an inner peripheral wall of the gas-phase portion or an inner peripheral wall of the liquid-phase portion by activating the pump such that the gas is introduced into or discharged from the gas-phase portion.

10. The adjusting device for the pressure detector according to claim 3, further comprising a first pressure-detecting unit that detects a pressure in the first zone.

11. The adjusting device for the pressure detector according to claim 5, wherein the pump is a peristaltic pump capable of sending the gas by squeezing the piping in a lengthwise direction of the piping.

12. The adjusting device for the pressure detector according to claim 6, wherein the adjusting-pressure-acquiring unit calculates the adjusting pressure in accordance with the relationship between the pressure and the capacity of the first zone in the first step and the pressure and the capacity of the combination of the gas-phase portion, the first zone, and the second zone in the second step.

13. The adjusting device for the pressure detector according to claim 7, wherein the adjusting-pressure-acquiring unit calculates an actual capacity of the first zone or the second zone in accordance with the relationship between the pressure and the capacity of the first zone in the first step and the pressure and the capacity of the combination of the gas-phase portion, the first zone, and the second zone in the second step.

* * * * *